US010434270B2

(12) United States Patent
Isaza

(10) Patent No.: US 10,434,270 B2
(45) Date of Patent: Oct. 8, 2019

(54) COMPENSATION OF BREATH DELIVERY

(71) Applicant: KONINKLIJKE PHILIPS N.V., Eindhoven (NL)

(72) Inventor: Fernando Jose Isaza, Carlsbad, CA (US)

(73) Assignee: Koninklijke Philips N.V., Eindhoven (NL)

(*) Notice: Subject to any disclaimer, the term of this patent is extended or adjusted under 35 U.S.C. 154(b) by 785 days.

(21) Appl. No.: 14/368,674

(22) PCT Filed: Dec. 11, 2012

(86) PCT No.: PCT/IB2012/057177
§ 371 (c)(1),
(2) Date: Jun. 25, 2014

(87) PCT Pub. No.: WO2013/098686
PCT Pub. Date: Jul. 4, 2013

(65) Prior Publication Data
US 2015/0000665 A1    Jan. 1, 2015

Related U.S. Application Data

(60) Provisional application No. 61/580,328, filed on Dec. 27, 2011.

(51) Int. Cl.
*A61M 16/00* (2006.01)

(52) U.S. Cl.
CPC ...... *A61M 16/0003* (2014.02); *A61M 16/026* (2017.08); *A61M 2016/0027* (2013.01); *A61M 2016/0036* (2013.01); *A61M 2016/0042* (2013.01); *A61M 2205/15* (2013.01); *A61M 2205/3362* (2013.01); *A61M 2205/50* (2013.01); *A61M 2230/46* (2013.01)

(58) Field of Classification Search
CPC .......... A61M 16/0003; A61M 16/0051; A61M 16/0036; A61M 2205/15; A61M 2205/50; A61M 2016/0042; A61M 2016/0027
See application file for complete search history.

(56) References Cited

U.S. PATENT DOCUMENTS

| 3,599,633 A | 8/1971 | Beasley |
| 3,729,000 A | 4/1973 | Bell |
| 3,834,381 A | 9/1974 | Peterson |

(Continued)

FOREIGN PATENT DOCUMENTS

EP    1005829 A1    6/2000

OTHER PUBLICATIONS

Respironics: Project Esprit: "Controls Design Specification"; Document No. V00267SP, Sep. 4, 2007, 106 Page Document.

*Primary Examiner* — Peter S Vasat
*Assistant Examiner* — Margaret M Luarca

(57) ABSTRACT

The present invention relates to a method of delivering gas during ventilation of a patient using a system for breath delivery. The method of gas delivery includes real-time compensation of gas compression losses, in the current breath delivery phase, and gas leakage losses. The present invention further relates to a system for breath delivery. Still further, the present invention relates to a computer implemented method adapted of delivering gas during ventilation of a patient using a system for breath delivery.

9 Claims, 7 Drawing Sheets

(56) References Cited

U.S. PATENT DOCUMENTS

| | | | |
|---|---|---|---|
| 3,923,056 A | 12/1975 | Bingmann et al. | |
| 6,142,150 A | 11/2000 | O'Mahoney | |
| 6,557,553 B1 | 5/2003 | Borrello | |
| 7,886,739 B2 | 2/2011 | Soliman et al. | |
| 7,918,223 B2 | 4/2011 | Soliman et al. | |
| 9,114,220 B2 | 8/2015 | Masic | |
| 9,155,852 B2 | 10/2015 | Soliman et al. | |
| 2007/0157930 A1 | 7/2007 | Soliman et al. | |
| 2009/0293876 A1* | 12/2009 | Soliman | A61M 16/0096 128/204.22 |
| 2009/0301486 A1* | 12/2009 | Masic | A61B 5/08 128/204.21 |
| 2010/0147303 A1 | 6/2010 | Jafari | |
| 2010/0236555 A1 | 9/2010 | Jafari | |
| 2011/0196251 A1 | 8/2011 | Jourdain | |
| 2013/0192600 A1* | 8/2013 | Eklund | A61M 16/0051 128/204.23 |

* cited by examiner

COMPENSATION OF BREATH DELIVERY

CROSS-REFERENCE TO PRIOR APPLICATIONS

This application is the U.S. National Phase application under 35 U.S.C. § 371 of International Application No. PCT/IB2012/057177, filed on Dec. 11, 2012, which claims the benefit of U.S Provisional Patent Application No. 61/580,328, filed on Dec. 27, 2011. These applications are hereby incorporated by reference herein.

FIELD OF THE INVENTION

The present invention relates to a method and system for compensation of breath delivery. The method and system is usable for volume ventilation mode in anesthesia ventilators as well as ICU ventilators, and other ventilators which require accurate volume delivery to the patient's lungs.

BACKGROUND OF THE INVENTION

When a patient is in need of being connected to a breath delivery system, e.g. during an operation or when in a coma, or for any other reason is in need of assisted breathing, the patient is attached to the system. When a ventilator is operating in a volume control mode, a prescribed tidal volume is specified for delivery to the patient. However, the pressure in the patient's lungs in increases when gas is introduced by the ventilator and this can only happen if the pressure in the tubing system is greater than the pressure in the lungs. Thus the tubing system must be pressurized in order to deliver gas to the patient lungs. The process of pressurization requires that a volume of gas be delivered to the tubing system. Therefore, to deliver a predetermined amount of gas to the patient's lungs requires the ventilator to deliver that predetermined amount of gas plus the volume of gas required to pressurize the tubing system to the levels required for gas to be transferred from the tubing system to the patient's lungs.

U.S. Pat. No. 6,142,150 discloses one type of gas delivery concept.

The inventor of the present invention has appreciated that an improved breath delivery system is of benefit, and has in consequence devised the present invention.

SUMMARY OF THE INVENTION

Generally in some systems an operator inputs a prescribed tidal volume to a system. Because initially only the prescribed tidal volume is delivered to the Patient-Tubing system, the patient receives less than the prescribed tidal volume as some of the volume delivered by the ventilator is used in pressurizing of the Patient-Tubing pneumatic compliance of the system. That is, as a gas volume is delivered to a Patient-Tubing system, the pressure in the circuit increases and the volume delivered to the patient is less than prescribed. In order to compensate for the gas used to pressurize the Patient-Tubing pneumatic compliance, the ventilator determines the volume associated with pressurization of the system at the end of the delivery phase via the product of the tubing circuit compliance and the end of inhalation pressure. Thus, after the completion of the breath, the volume used by the tubing circuit is then added to the input volume on the next patient inspiration. However, because the added volume is translated into a Peak Flow change (since the inspiration time must remain constant), the pressure during the delivery phase increases to a new level thus the added amount is insufficient to ensure delivery of the prescribed volume. The process repeats during the following breaths, on which the tubing volume is again determined, and after some iterations (the number of which depends on the patient characteristics and the tubing system compliance) the tidal volume is actually delivered to the patient.

It would be advantageous to devise a system and/or method where these problems are avoided. It would also be desirable to enable a health care person to make use of a system carrying out fast compensation of gas losses in ventilating system for patients. In general, the invention preferably seeks to mitigate, alleviate or eliminate one or more of the above mentioned disadvantages singly or in any combination. In particular, it may be seen as an object of the present invention to provide a method that solves the above mentioned problems, or other problems, of the prior art.

To better address one or more of these concerns, in a first aspect of the invention a method of delivering gas during ventilation of a patient is presented that uses a system for breath delivery comprising a Patient-Tubing system coupled with an outlet of a gas delivery system for conveying gas to a patient during gas-supplemented inhalations; a flow sensor coupled with said outlet for sensing the gas flow, a Patient-Tubing system pressure sensor coupled with said Patient-Tubing system for sensing gas pressure therein and providing Patient-Tubing system pressure signals representative thereof; a processor, or processing unit, coupled with said sensors and operable for receiving said signals therefrom, said processor operable to determine, using said received signals, the amount of gas needed to compensate for gas lost in pressurization of the Patient-Tubing system and gas lost through leakages in the Patient-Tubing system. The method may comprise the steps of: obtaining in one sample flow information from said flow sensor, obtaining in the one sample pressure information from said Patient-Tubing system pressure sensor, and calculating for the one sample, based on the flow information from said flow sensor and pressure information from said Patient-Tubing system pressure sensor, the amount of gas needed to compensate for gas lost in pressurization of the Patient-Tubing system and gas lost through leakages in the Patient-Tubing system. Note that gas may be lost in the Patient-Tubing circuit or deliberately through the exhalation valve or through leakages around the endotracheal tube, and not just at the interface between the Patient-Tubing system and the patient.

A second aspect of the present invention relates to a system for breath delivery comprising a Patient-Tubing system coupled with an outlet of a gas delivery system for conveying gas to a patient during gas-supplemented inhalations; a flow sensor coupled with said outlet for sensing the gas flow, a Patient-Tubing system pressure sensor coupled with said Patient-Tubing system for sensing gas pressure therein and providing Patient-Tubing system pressure signals representative thereof; a processor coupled with said sensors and operable for receiving said pressure signal and flow signal therefrom, said processor operable to determine, using said received signals, the amount of gas needed to compensate for gas lost in pressurization of the Patient-Tubing system and gas lost in interface between Patient-Tubing system and patient, the processor may be arranged for obtaining in one sample flow information from said flow sensor, the processor arranged for obtaining in the one sample pressure information from said Patient-Tubing system pressure sensor, the processor arranged for calculating for the one sample, based on the flow information from said flow sensor and pressure information from said Patient-Tubing system pressure sensor, the amount of gas needed to compensate for gas lost in pressurization of the Patient-Tubing system and gas lost through leakages in the Patient-Tubing system. As mentioned above, gas may also be lost in the Patient-Tubing circuit or deliberately through the exhalation valve or through leakages around the endotracheal tube, and not just at the interface between the Patient-Tubing system and the patient.

During ventilation, the gas delivery system injects gas into the Patient-Tubing system causing it to pressurize and in turn, this pressurization drives the gas into the patient's airway and ultimately into his/her lungs. During Volume Control Ventilation, the goal is to deliver a predetermined volume of gas into the patient lungs using a predetermined flow rate and/or a predetermined duration. The techniques used in prior art require more than one breath (typically many breaths) to achieve proper, stable, compensation for the gas losses in the system and when the patient is agitated or there are disturbances in the tubing system, the instability caused by these conditions makes the compensation less accurate. The present invention solves or at least alleviates these problems by implementing the compensation on a sample by sample basis on the particular breath being delivered, regardless of the stability conditions.

In both the first and second aspect the calculation of the needed compensation is done on a sample by sample basis.

After having determined the amount of gas needed to compensate for gas lost in pressurization of the Patient-Tubing system and gas lost through leakages in the Patient-Tubing system, the system and method may include using this for compensating the delivered amount of gas flow to the patient. In alternative embodiments the flow at the airway inlet could be estimated instead of being measured, e.g. using sensors at the outlet of a ventilator and estimating the flow lost in the tubing due to compressibility of the gases, estimating the gas lost through leakages, measuring the gas through the exhalation flow sensor, and the pressure at the airway entrance by use of estimated flow though the tubing circuit limbs and using also estimation of the resistance of these limbs, and their associated pressure drops.

Advantageously the first aspect may further include the following features.

Advantageously the step of calculating the amount of gas needed to compensate gas loss may include determining an estimate for leakages in the the patient-tubing system, which comprises the tubing circuit, the patient's airways and the patient's lungs. By determining an estimate for gas leakages the calculation may compensate for these gas losses, which again is of benefit for the patient. These gas losses may change due to movement of the patient, such as cough or the patient being moved a bit by a health care person. By determining these gas losses on a sample-by-sample basis, the method may fast correct the compensation as required.

Advantageously the method may comprise an initial step of an operator supplying a gas flow target. The method may also comprise the step of calculating the amount of gas needed to compensate gas loss, which includes determining compensation to reach said target gas flow.

Advantageously the method is performed every breath. By performing the method on every breath the need for the patient to wait more than one breath (typically many breaths) to achieve proper compensation for gas losses, is eliminated.

Advantageously the compensation may be based on the equation:

$Q_{tube} = C_{tube} \times dP_y/dt$, where $Q_{tube}$ is tubing gas flow, $C_{tube}$ is tubing compliance and $P_y$ is tubing circuit wye pressure, and $dP_y/dt$ is the derivative of $P_y$. The present invention uses this equation on a sample by sample basis to calculate Qtube in real time. $P_y$ is required to be available for the compensation to be properly performed using this equation. Also, the ventilator flow needed to achieve the user set PF at the entrance of the patient's lungs (i.e. $Q_L$) may be determined. Thus at each sample interval, $Q_v$ is determined.

Advantageously the compensation for flow lost due to leakages in the tubing system and/or the airway and/or the lung includes the equation:

$$Q_v(n) = PF(n) + Q_{exh}(n) + K_o \times (P_y(n))_m + K_1 \times (P_{AW}(n))^m + K_2 \times (P_{Lung}(n))_m + C_{tube} \times dP_y(n)/dt \qquad \text{Equation 8}$$

Where:
PF(n)=is the value of the peak flow waveform set by the user, for the control interval n.
$Q_{exh}(n)$=is the value of the exhalation flow sensor reading, for the control interval n.
$K_o$=is the conductance for the equivalent orifice representing the tubing circuit leak, for the control interval n.
m=exponent (which depends on the leak model but is typically around 0.6),
$P_y(n)$=is the value of the tubing circuit pressure, for the control interval n.
$K_1$=is the conductance for the equivalent orifice representing the Lung leak, for the control interval n.
$P_{AW}(n) = P_y(n) - R_{ET} \times Q_{AW}$=the value of the airway pressure, for the control interval n.
$P_{Lung}(n) = P_{AW}(n) - R_L \times Q_o$=the value of the lung pressure, for the control interval n.
$P_{mus}(n)$=Patient's muscles pressure, for the control interval n.
$C_{tube}$=is the value of the tubing circuit compliance.
$dP_y(n)/dt$=is the value of the tubing circuit pressure slope/derivative, for the control interval n.

Advantageously the compensation for total leakage loss includes the equations:

$$Q_{v(n)} = Q_{tube(n)} + Q_{L(n)} + Q_{exh(n)} + Q_{Total\_Leak(n)} \text{ and}$$

$$Q_{v(n)} = PF_{(n)} + Q_{exh(n)} + K \times (Po(n))^m + C_{tube} \times dP_{y(n)}/dt$$

wherein $Q_{v(n)}$ as a desired flow target, $Q_{tube}$ is tubing gas flow, $Q_L$ is lung gas flow, $Q_{exh}$ is exhalation gas flow, $Q_{Total\_Leak}$ is the total gas flow leak, where $Q_{Total\_Leak(n)} = K \times (P_{o(n)})^m$, $PF_{(n)}$ is a value of the peak flow waveform set by an operator, K is the conductance for the equivalent orifice representing the total gas flow leak, $P_o$ is the pressure at the pertinent pressure site where the leak is assumed to be located, $C_{tube}$ is tubing compliance, and $P_y$ is tubing circuit wye pressure.

Advantageously the system according to the second aspect of the present invention may include the following features.

Advantageously the processor, or processing unit, may be constituted by a combination of a signal processor and a general purpose processor, wherein the signal processor is arranged for obtaining signals from the flow sensor and the Patient-Tubing system pressure sensor and the general processor is arranged for performing the calculations. By having a dedicated signal processor and a general purpose processor the operations of the two parts may be optimized. The general purpose processor may be any type of processor, e.g. commonly a computer processor or the like. Examples include x86-type architecture processors or the like. Signal processors provide sampling of signals from sensors and optimized processing of such signals.

Advantageously the system may comprise an input unit configured to receive a target gas flow, and the processor is adapted for calculating the amount of gas needed to compensate gas loss including determining compensation to reach said target gas flow. It would be advantageous that an operator, e.g. a health care person, could input a target value for the system to deliver. The system would then be able to calculate the optimal compensation. The input unit could be a keyboard, pointing device, a portable device having a dedicated input and having a wireless or wired connection to the system.

A third aspect of the present invention relates to a computer implemented program adapted for performing the steps of the method according to the first aspect of the present invention on a system according to the second aspect of the present invention.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which FIG. 1 schematically illustrates a breath curve.

DESCRIPTION OF EMBODIMENTS

Figure 1:
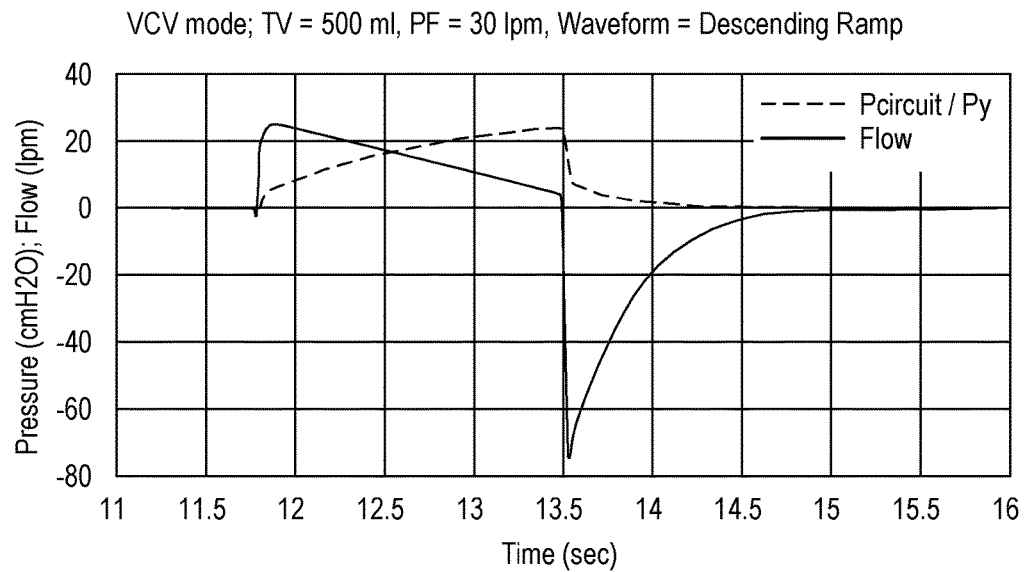

FIG. 1 schematically illustrates a breath curve. During ventilation, a ventilator injects gas into a tubing system connected to a patient, causing it to pressurize and in turn, this pressurization drives the gas into the patient's airway and ultimately into his/her lungs. During Volume Control Ventilation, the objective is to deliver a predetermined volume of gas into the patient lungs using a predetermined flow rate and a predetermined duration. The predetermined flow rate may have a particular shape/waveform such as a square or a descending ramp or a forward phased sinusoidal waveform, also the waveform could be any other type of waveform offered by the system or device. FIG. 1 illustrates a descending ramp waveform with the associated tubing circuit pressure waveform.

In the absence of leakages in the tubing system or the lungs, the problem of accurate volume delivery into the patient's lung may be better explained by examination of the simplified Ventilator-Patient-Tubing pneumatic model that appears in FIG. 2 and discussed below.

Figure 2:
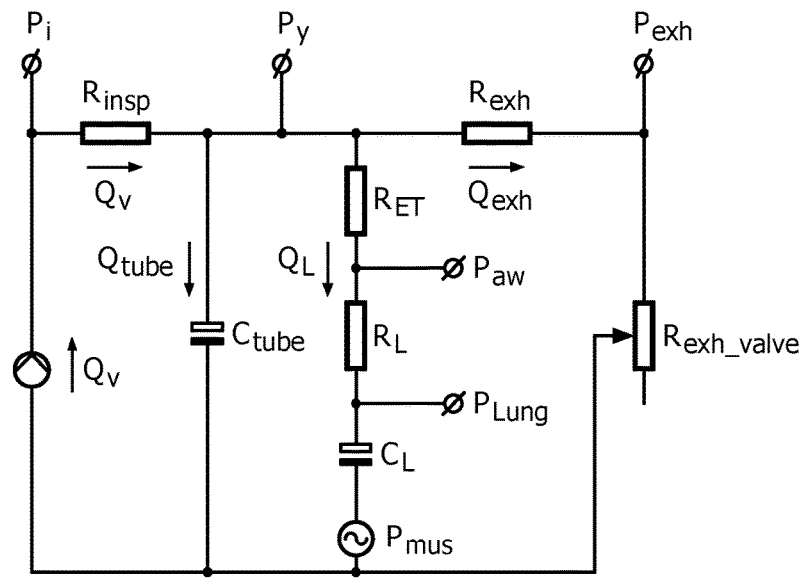
FIG. 2 is a schematic illustration of a simplified Ventilator-Patient-Tubing pneumatic model.

In FIG. 2 the following definitions are used:
$P_i$=inhalation pressure sensor $P_e$=exhalation pressure sensor $P_y$=tubing circuit wye Pressure
$P_{aw}$=airway pressure $P_{Lung}$=lung pressure $P_{mus}$=patient's muscles pressure
$Q_v$=ventilator gas flow $Q_{tube}$=tubing gas flow $Q_L$=lung gas flow $Q_{exh}$=exhalation gas flow
$R_{insp}$=inspiratory limb resistance $R_{exh}$=expiratory limb resistance $R_{ET}$=ET tube resistance
$R_L$=lung resistance $R_{exh\ valve}$=exhalation valve resistance $C_{tube}$=tubing compliance $C_L$=lung compliance From this model, it is possible to derive the relationship that links the different flows that are used in the system during ventilation. That is:

$$Q_v = Q_{tube} + Q_L + Q_{exh} \quad \text{Equation 1}$$

Since one objective in Volume Control Ventilation is to deliver a predetermined volume of gas into the patient lungs using a predetermined flow rate and/or a predetermined duration, then that means that $Q_L$ must possess these characteristics. However, when the user, i.e. health care person, sets the tidal volume (Tv) and the peak flow (PF) level, the ventilator does not know how much tubing volume is going to be required to pressurize the tubing system, as it is a function of the maximum tubing circuit wye pressure level ($P_y$) developed and this pressure is only known at the end of the gas delivery phase.

Related algorithms compute the volume used by the tubing once the gas delivery phase is over, via use of the equation 2 below, and add this volume to the tidal volume (Tv) set originally and then computes again the PF using this new Tv, while keeping the gas delivery phase duration (Ti) constant, and iterate this process on a breath to breath basis. If and when the pressure ($P_y$) stabilizes (may be a function of patient activity), the volume intended for delivery to the patient lungs is finally obtained.

$$\text{Tubing\_volume} = C_{tube} \times P_y \quad \text{Equation 2}$$

This process typically takes from 10 to 15 breaths to achieve stability when there is no patient activity and depends on the patient lung and airway characteristics as well as the level of patient activity.

The present invention transforms equation 2 by taking the derivative on both equation sides and since the derivative of volume is flow, obtains equation 3 below.

$$Q_{tube} = C_{tube} \times dP_y/dt \quad \text{Equation 3}$$

The present invention uses equation 3, on a sample by sample basis to calculate $Q_{tube}$ in real time, since we have always access to the $P_y$ signal, and then recalculates the ventilator flow needed to achieve the user set PF at the entrance of the patient's lungs (i.e. QL). Thus at each sample interval, $Q_v$ is determined as the discrete equation below indicates.

$$Q_v(n) = Q_{tube}(n) + Q_L(n) + Q_{exh}(n) \quad \text{Equation 4}$$

Where n is the sample/control interval number, $Q_{exh}(n)$ is the value of the exhalation flow sensor reading for the control interval n, $Q_{tube}(n)$ is the value of the tubing flow estimate for the control interval n.

To properly compensate for gas loss in the tubing, due to gas compression, $Q_L(n)$ is then set to be equal to the PF set by the user and having the waveform characteristic set by the user. Also note that $Q_{exh}(n)$ is typically zero, but can be any flow measured during the gas delivery phase. Finally, as explained above, $Q_{tube}(n)$ is estimated using equation 3, namely $Q_{tube}(n) = C_{tube} \times dP_y(n)/dt$ where $dP_y(n)/dt$ is the value of the tubing circuit pressure slope/derivative for the control interval n. $Q_v(n)$ is then updated every control interval during the gas delivery phase and used as the gas delivery control system target therefore reflecting the gas needed to compensate for the flow lost in pressurizing the tube as well as for the flow lost through the exhalation valve (if different from zero).

Figure 3:
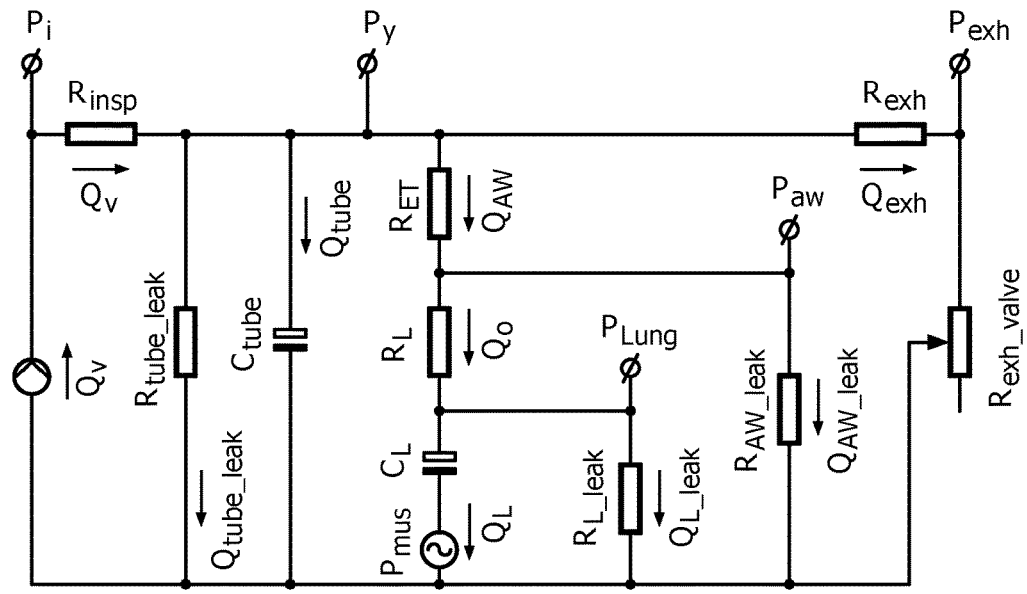
FIG. 3 is a schematic diagram illustrating the Patient-Tubing pneumatic system including the different leak flows, FIGS. 4-9 schematically illustrates results of simulations, FIGS. 10-11 schematically illustrates breath curves, FIG. 12 schematically illustrates steps of a method according to the present invention, and FIG. 13 schematically illustrates a system according to the present invention.

The method according to the present invention may include extending Equation 1 to account for flow lost due to leakages in the tubing system and/or the airway (cuff deflated) and/or the lung (possibly due to a fistula). A pre-requisite for this operation is that these leakages can be characterized and estimated (via estimation of $C_L$, $R_L$ and the $P_{AW}$, $P_{Lung}$ and $P_{mus}$ pressures). The schematic diagram in FIG. 3 illustrates the Patient-Tubing pneumatic system including the different leak flows.

The relationships between $Q_{AW}$ and $Q_{AW\_leak}$, $Q_L$ and $Q_{L\_leak}$ as we as those between $Q_V$, $Q_{tube}$, $Q_{tube\_leak}$, $Q_{exh}$, and $Q_{AW}$ are expressed below in equations 5a, 5b and 5c.

$$Q_{AW} = Q_o + Q_{AW\_leak} \quad \text{Equation 5a}$$

$$Q_o = Q_L + Q_{L\_leak} \quad \text{Equation 5b}$$

$$Q_v = Q_{tube} + Q_{AW} + Q_{exh} + Q_{tube\_leak} \quad \text{Equation 5c}$$

Equation 6 below reflects these flow elements. Since the leakages in the tubing system and the lung are pressure dependent, it is possible to calculate the tubing and/or the lung leakages in real time and compensate the gas delivery so the intended PF is delivered to the lung.

$$Q_v = Q_{tube} + Q_L + Q_{exh} + Q_{tube\_leak} + Q_{AW\_leak} + Q_{L\_leak} \quad \text{Equation 6}$$

In discrete form, equation 6 becomes $$Q_v(n) = Q_{tube}(n) + Q_L(n) + Q_{exh}(n) + Q_{tube\_leak}(n) + Q_{AW\_leak}(n) + Q_{L\_leak}(n) \quad \text{Equation 7}$$

Note that $Q_{tube\_leak}$ is a function of $P_y$, $Q_{AW\_leak}$ is a function of $P_{AW}$ and $Q_{L\_leak}$ is a function of $P_{Lung}$.

Although it is not part of this invention, $Q_{AW\_leak}$, $Q_{tube\_leak}$ and $Q_{L\_leak}$ are typically expressed (although other leak models may be used) in terms of the corresponding pressures as appears below.

$$Q_{tube\_leak}(n) = K_o \times (P_y(n))^m \quad \text{Equation 7a}$$

$$Q_{AW\ leak}(n) = K_1 \times (P_{AW}(n))^m \quad \text{Equation 7b}$$

$$Q_{Lung\_leak}(n) = K_2 \times (P_{Lung}(n))^m \quad \text{Equation 7c}$$

The equation 7 is implemented in discrete time as indicated by the equation below.

$$Q_v(n) = PF(n) + Q_{exh}(n) + K_o \times (P_y(n))^m + K_1 \times (P_{AW}(n))^m + K_2 \times (P_{Lung}(n))^m + C_{tube} \times dP_y(n)/dt \quad \text{Equation 8}$$

Where:
PF(n)=is the value of the peak flow waveform set by the user, for the control interval n.
$Q_{exh}(n)$=is the value of the exhalation flow sensor reading, for the control interval n.
$K_o$=is the conductance for the equivalent orifice representing the tubing circuit leak, for the control interval n.
m=exponent (depends on the leak model but is typically around 0.6)
$P_y(n)$=is the value of the tubing circuit pressure, for the control interval n.
$K_1$=is the conductance for the equivalent orifice representing the Lung leak, for the control interval n.
$P_{Aw}(n) = P_y(n) - R_{ET} \times Q_{AW}$=the value of the airway pressure, for the control interval n.
$P_{Lung}(n) = P_{AW}(n) - R_L \times Q_o$=the value of the lung pressure, for the control interval n.

$P_{mus}(n)$=patient's muscles pressure, for the control interval n. $C_{tube}$=is the value of the tubing circuit compliance.
$dP_y(n)/dt$=is the value of the tubing circuit pressure slope/derivative, for the control interval n. The term control interval refers to the interval where control is carried out. The control interval has a specific length, as opposed to the sample interval which could be of different length etc.

Note that estimation of $C_L$, $R_L$, $P_y$, $P_{AW}$ and $P_{Lung}$ are not discussed here. Estimation of $K_o$, $K_1$ and $K_2$ are not discussed here either as this is thoroughly understood by those skilled in the subject of leak estimation.

Thus complete compensation for flow losses occurring in the tubing circuit (due to gas compression or leaks or both) as well as flow losses due to leakages at the patient's airway or lungs or both is achieved by using the results of the calculation of equation 8, on a control interval by control interval basis and using the resulting $Q_v(n)$ as the desired flow target used by the flow controller responsible for control of the gas delivery output for the ventilator.

Lastly, if it is only possible to characterize the Total leakage, equations 7 & 8 can be changed to reflect that as appears below, but the principle of compensation on a sample by sample basis remains.

$$Q_v(n) = Q_{tube}(n) + Q_L(n) + Q_{exh}(n) + Q_{Total\_Leak}(n) \quad \text{Equation 9}$$

$$Q_v(n) = PF(n) + Q_{exh}(n) + K \times (P_0(n))^m + C_{tube} \times dP_y(n)/dt \quad \text{Equation 10}$$

Where:
K=is the conductance for the equivalent orifice representing the Total leak, for the control interval n.
$P_o$=the value of the pressure, at the pertinent pressure site where the leak is assumed to be located, for the control interval n.

This last part of the compensation method is likely to be the most common one as it highly difficult to accurately estimate the different leakages even when prior knowledge of the leak sites are known. It is usually the case that during ventilation, the major leak occurs at the patient port site (as in non-invasive ventilation), but it is also common to find leakages at the airway (during invasive ventilation with the Endotracheal tube's cuff deflated). For these cases the $P_o$ pressure measurements would be assumed to be at the wye ($P_y$) and the airway ($P_{AW}$) respectively.

Compensation for leakages, using the method of the present invention, avoids the iterative process associated with the use of volume feedback to compensate for the volume lost through the leak orifice(s) as well as the need for pressure stability in the system.

The six graphs in FIGS. 4-9 illustrate, via depiction of the different flow and volume traces, the differences between no compliance or leak compensation, and the performance of the compliance compensation method being disclosed when no leaks are compensated for and when leaks are present and are compensated for.

Figure 4:
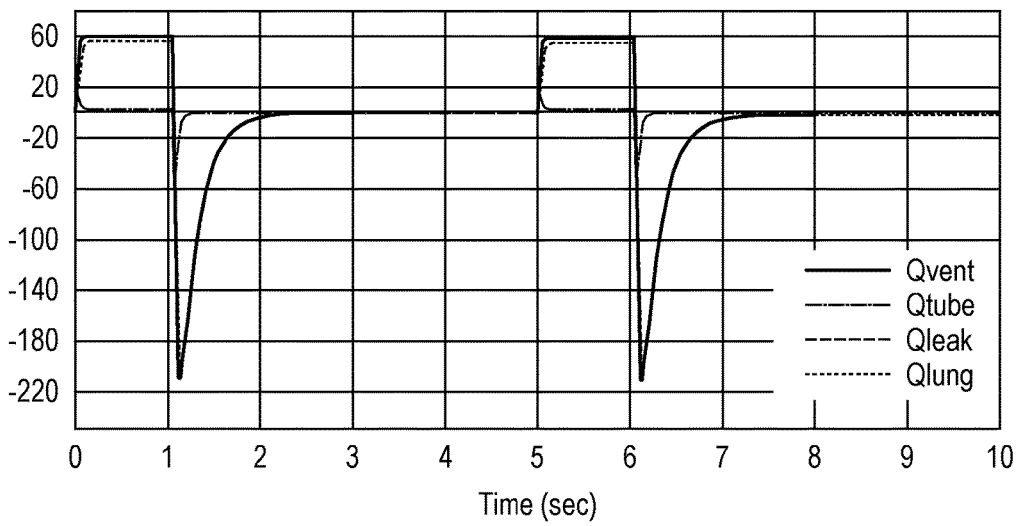

In FIG. 4 the result of a simulation is illustrated. Note that the flow delivered by the ventilator ($Q_{vent}$), in steady state, is equal to the peak flow setting but the lung flow trace ($Q_{Lung}$) is NOT.

The settings for ventilation are:
Peak Flow=60 lpm, Tidal Volume=1000 ml and Respiratory rate=12 bpm;
And the Tubing Compliance=2 ml/cmH$_2$O. For demonstration purposes, the leak is assumed to occur in the tubing circuit.

Figure 5:
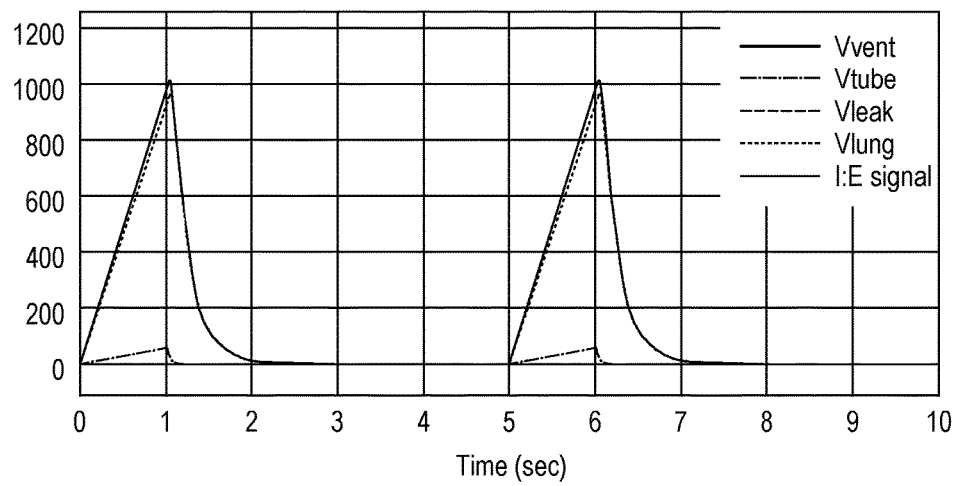

In FIG. 5 the volume delivered by the ventilator ($V_{vent}$) was 1000 ml while the volume delivered to the patient was 947.17 ml.

Note: The I:E signal is a signal designed to indicate the gas delivery phase of a breath. It is >0 during the gas delivery phase of a breath and it is 0 (zero) during the exhalation phase of the breath. Furthermore, it has been amplified so it equals the Tidal Volume setting for ease of graphical assessment of the delivery accuracy.

Figure 6:
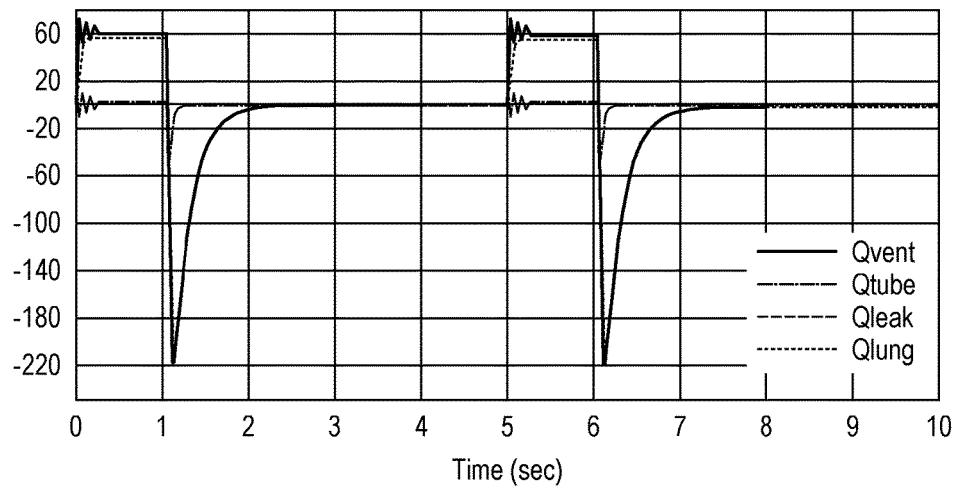

In FIG. 6 note that the lung flow trace ($Q_{Lung}$) is equal, in steady state, to the peak flow setting and the $Q_{vent}$ trace is hi higher than the set Peak Flow. The difference between $Q_{vent}$ and $Q_{Lung}$ is $Q_{tube}$.

Figure 7:
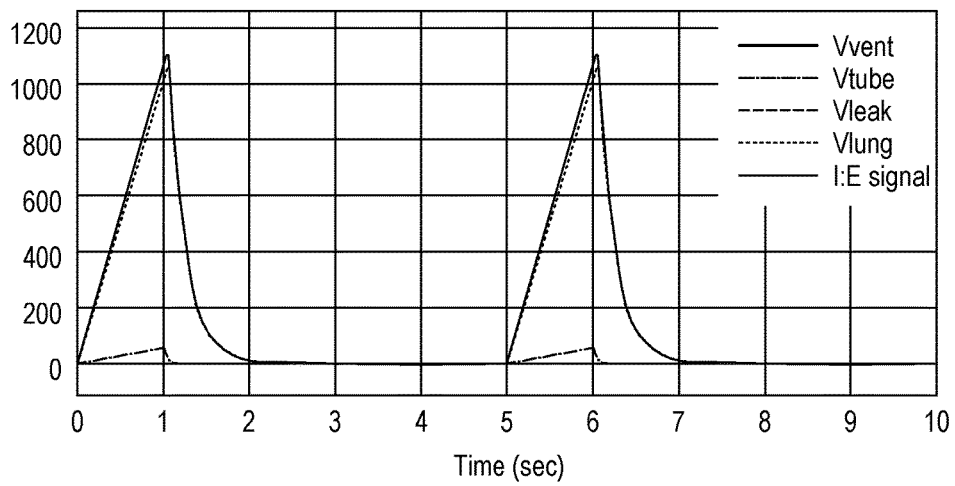

In FIG. 7 note that the volume delivered by the ventilator (Vvent) was more than 1000 ml while the volume delivered to the patient was 1004 ml. The reason why the lung volume continues to increase after the I:E signal has return to zero is that the lung flow remains positive for a little more as $Q_{vent}$ and $Q_{tube}$ also remain positive during that lapse (this can be attributed to the flow and exhalation valves responses).

Figure 8:
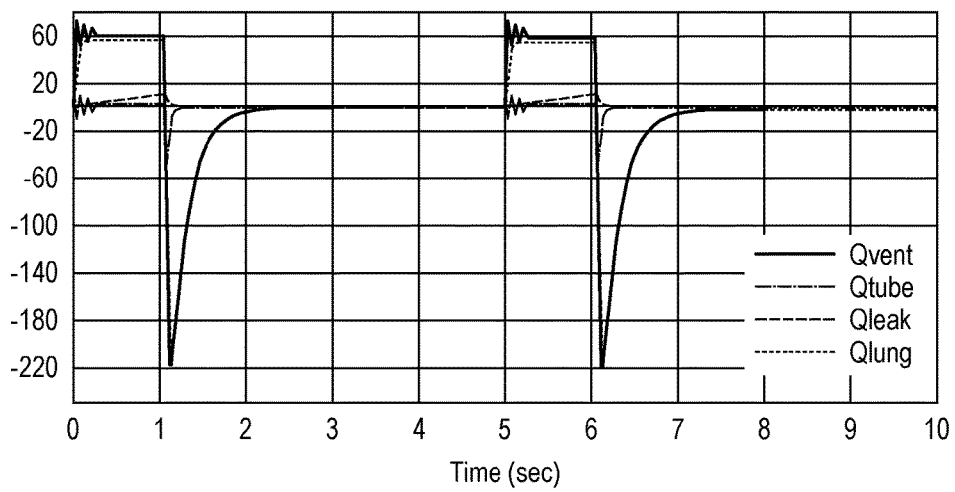

In FIG. 8 Note that the lung flow trace ($Q_{Lung}$) is equal, in steady state, to the peak flow setting and the $Q_{vent}$ trace is higher than the set peak flow. The difference between $Q_{vent}$ and $Q_{Lung}$ is $Q_{tube}+Q_{leak}$.

Figure 9:
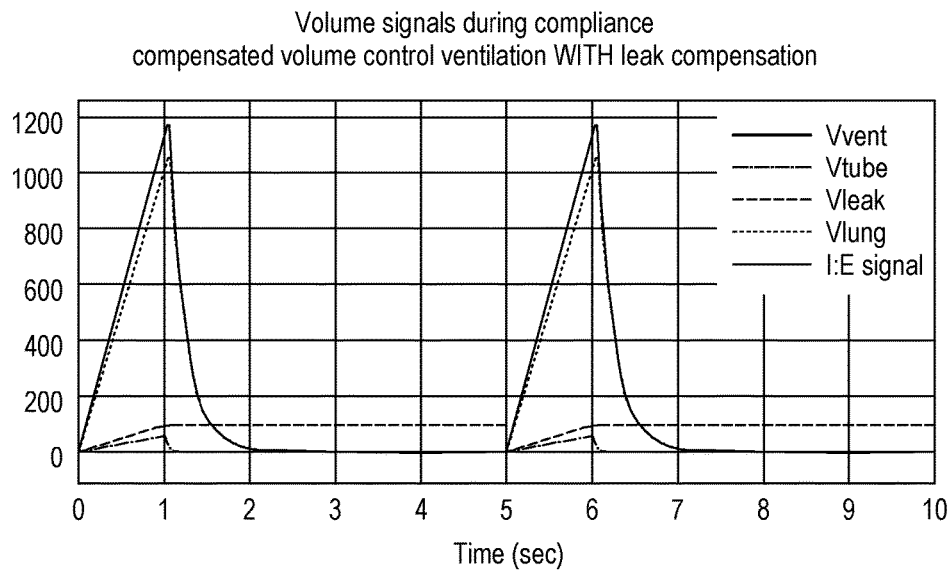

In FIG. 9 Note that the volume delivered by the ventilator ($V_{vent}$) was significantly more than 1000 ml while the volume delivered to the patient was 1004 ml. The volume leaked was a little lower than 100 ml, as may be observed from the graph by looking at the cyan trace at the point where the I:E signal becomes zero (0).

Figure 10:
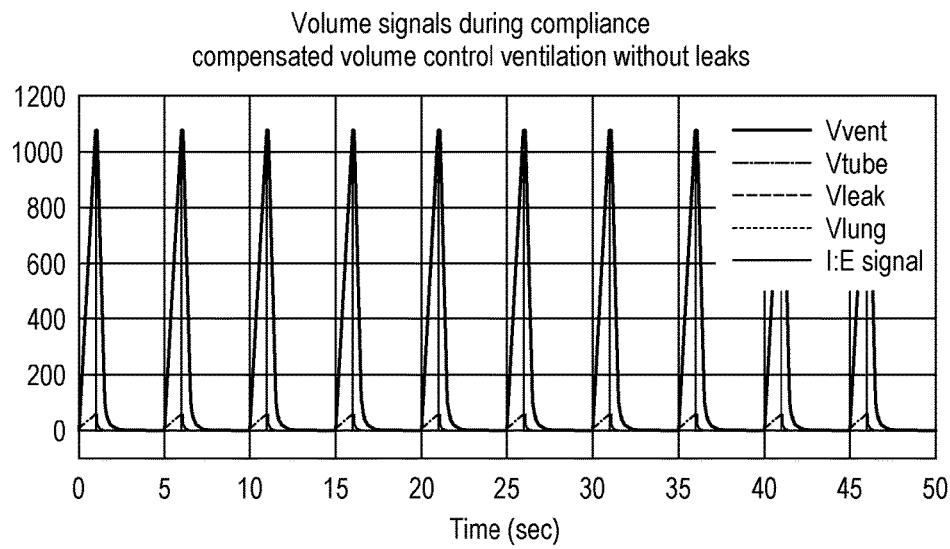
Figure 11:
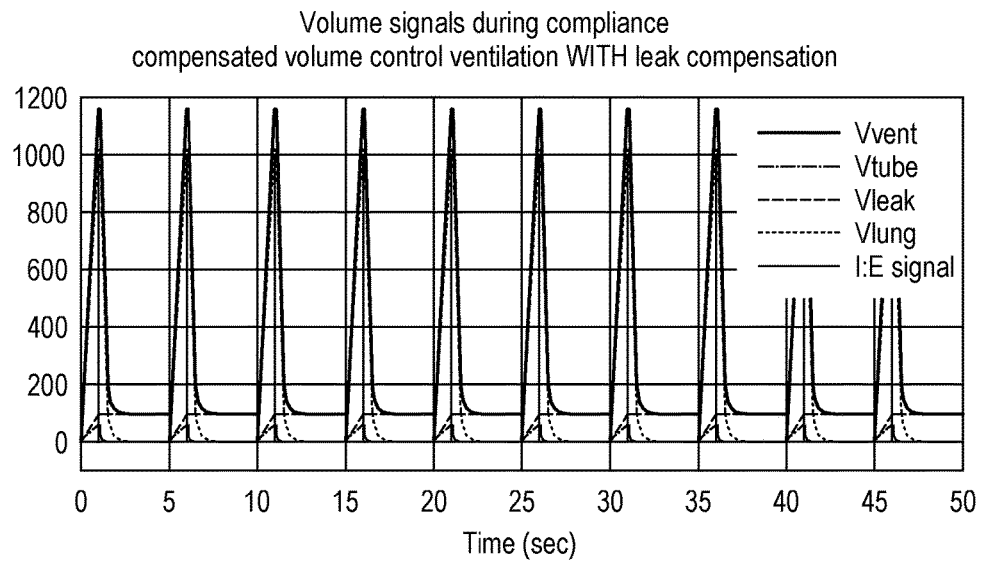

In FIGS. 10 and 11, the graphs illustrate that ALL breaths are similar to the first breath which demonstrates that no prior knowledge of the pressure level at the end of the delivery phase is needed for proper tubing compliance or leak compensation. For leak compensation, knowledge of the leak model is required for accurate compensation of the leak flow (not part of this invention), but the compensation algorithm does not make use of prior knowledge of the volume lost through the leak orifice(s) in order to carry out the compensation for the leaks. As explained before, both compensations are done via adjustment of the flow being delivered to the patient-tubing system while delivery is progressing.

Figure 12:
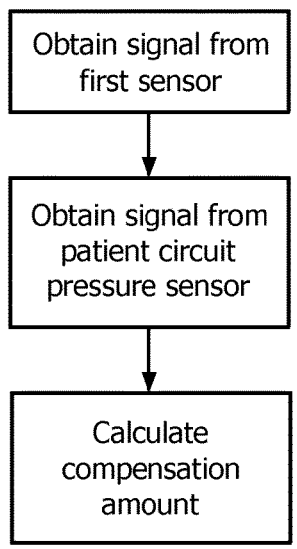

FIG. 12 schematically illustrates steps of a method according to the present invention. The method is performed on a system for breath delivery comprising a Patient-Tubing system coupled with an outlet of a gas delivery system for conveying gas to a patient during gas-supplemented inhalations; a flow sensor coupled with said outlet for sensing the gas flow, a Patient-Tubing system pressure sensor coupled with said Patient-Tubing system for sensing gas pressure therein and providing Patient-Tubing system pressure signals representative thereof; a processor coupled with said sensors and operable for receiving said pressure signals therefrom, said processor operable to determine, using said received pressure signals. The method comprises the step of obtaining in one sample pressure information from the flow sensor. The step of obtaining, in the one sample, pressure information from said Patient-Tubing system pressure sensor. And the step of calculating for the one sample, based on the information from said flow sensor and pressure information from said Patient-Tubing system pressure sensor, the amount of gas needed to compensate for gas lost in pressurization of the Patient-Tubing system and gas lost in interface between Patient-Tubing system and patient. Thereby the system is able to determine a new flow target for the flow controller, so as to deliver a compensated amount of gas.

In general terms the method for compensation comprises at least the steps of calculating or estimating the gas losses in the Patient-Tubing using measurements or estimation of the pressure(s) in the Patient-Tubing system, at the appropriate places as described elsewhere in the text. On each sample or control interval, the method comprises computation of the new flow target for the flow controller (i.e. Qv(n)). Further, the method comprises the step of controlling the gas flow, using the flow sensor internal to the ventilator, so that the new target is achieved.

The steps of the method may be repeated so as to create a control loop for a system monitoring and controlling a breath delivery system. Further steps may be performed in relation to the method as described elsewhere.

Figure 13:
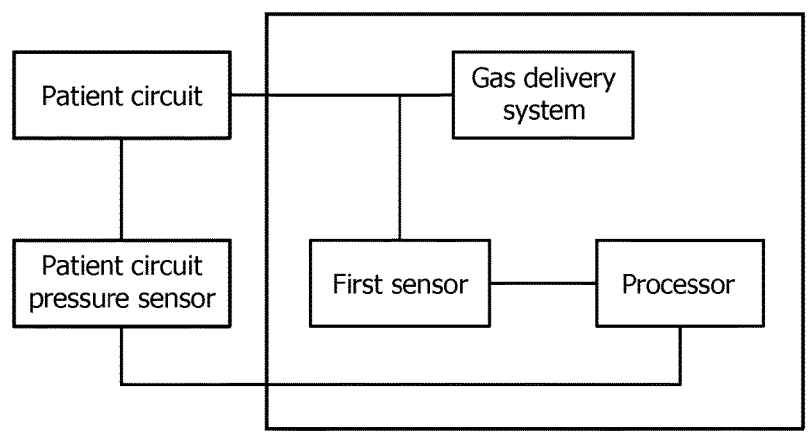

FIG. 13 schematically illustrates parts of a system according to the present invention. The system comprises a Patient-Tubing system coupled with an outlet of a gas delivery system for conveying gas to a patient during gas-supplemented inhalations. A flow sensor is coupled with the outlet for sensing the gas flow. A Patient-Tubing system pressure sensor is coupled with the Patient-Tubing system for sensing gas pressure therein and providing Patient-Tubing system pressure signals representative thereof. A processor is coupled with the sensors and operable for receiving the signals therefrom. The processor is operable in one sample, to obtain flow information from the flow sensor, and the processor is arranged for obtaining, in the one sample, pressure information from the Patient-Tubing system pressure sensor. Thereby the processor is able to, in one sample, to calculate, based on the flow information from the flow sensor and pressure information from the Patient-Tubing system pressure sensor, the amount of gas needed to compensate for gas lost in pressurization of the Patient-Tubing system and gas lost in interface between Patient-Tubing system and patient so as to obtain the above mentioned advantages.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for calculating, in real-time, an amount of gas during ventilation of a patient using a system for breath delivery comprising: a Patient-Tubing system coupled with an outlet of a gas delivery system for conveying gas to a patient during gas-supplemented inhalations; a flow sensor coupled with said outlet for sensing the gas flow; a Patient-Tubing system pressure sensor coupled with said Patient-Tubing system for sensing gas pressure therein and providing Patient-Tubing system pressure signals representative thereof; and a processor coupled with said sensors and operable for receiving said pressure and flow signals therefrom, said processor operable to perform, using said received pressure and flow signals, the method comprising the steps of:

obtaining, in each of a plurality of sample intervals, flow information from said flow sensor, wherein each sample interval is a breath;

obtaining, from each of the plurality of sample intervals, pressure information from said Patient-Tubing system pressure sensor;

calculating for each of the plurality of sample intervals, based on a compliance of the tubing and a calculated derivative of the pressure information from the Patient-Tubing system pressure sensor, a Patient-Tubing system flow; and continuously calculating in real-time for each of the plurality of sample intervals, based on the calculated Patient-Tubing system flow and on the flow information from the flow sensor, the amount of gas needed to compensate for gas lost in pressurization of the Patient-Tubing system and gas lost through leakages in the Patient-Tubing system;

wherein the compensation comprises the equation $Q_{tube}=C_{tube} \times dP_y/dt$, where $Q_{tube}$ is Tubing gas flow, $C_{tube}$ is Tubing compliance and $P_y$ is tubing circuit wye pressure; and wherein calculating the amount of gas needed to compensate gas loss comprises determining an estimate for leakages in the patient-tubing system, which comprises the tubing circuit, the patient's airways and the patient's lungs, wherein compensation for flow lost due to leakages in the tubing system and/or the airway and/or the lung utilizes conductance for the equivalent orifice representing the tubing circuit leak and/or the lung leak and/or the total gas flow leak.

2. The method according to claim 1, comprising an initial step of supplying, by an operator, a target gas flow, and further wherein the step of calculating the amount of gas needed to compensate gas loss comprises determining compensation to reach said target gas flow.

3. The method according to claim 1, wherein compensation for flow lost due to leakages in the tubing system and/or the airway and/or the lung comprises the equation:

$$Qv(n)=PF(n)+Q_{exh}(n)+K_o \times (P_y(n))^m+K_1 \times (P_{AW}(n))^m+K_2 \times (P_{Lung}(n))^m+C_{tube} \times dP_y(n)/dt$$

where:

PF(n)=is the value of the peak flow waveform set by the user, for the control interval n;

$Q_{exh}(n)$=is the value of the exhalation flow sensor reading, for the control interval n;

$K_o$=is the conductance for the equivalent orifice representing the tubing circuit leak, for the control interval n;

m=exponent;

$P_y(n)$=is the value of the tubing circuit pressure, for the control interval n;

$K_1$=is the conductance for the equivalent orifice representing the Lung leak, for the control interval n;

$P_{AW}(n)=P_y(n)-R_{ET} \times Q_{AW}$=the value of the Airway pressure, for the control interval n;

$P_{Lung}(n)=P_{AW}(n)-R_L \times Q_o$=the value of the Lung pressure, for the control interval n;

$P_{mus}(n)$=Patient's muscles pressure, for the control interval n;

$C_{tube}$=is the value of the tubing circuit compliance; and $dP_y(n)/dt$=is the value of the tubing circuit pressure slope/derivative, for the control interval n.

4. The method according to claim 1, wherein calculating the Patient-Tubing system flow comprises the equations:

$$Q_{v(n)}=Q_{tube(n)}+Q_{L(n)}+Q_{exh(n)}+Q_{Total\_Leak(n)} \text{ and}$$

$$Q_{v(n)}=PF_{(n)}+Q_{exh(n)}+K \times (P_o(n))^m+C_{tube} \times dP_{y(n)}/dt$$

wherein $Q_{V(n)}$ as a desired flow target, $Q_{tube}$ is Tubing gas flow, $Q_L$ is Lung gas flow, $Q_{exh}$ is Exhalation gas flow, $Q_{Total\_Leak}$ is the total gas flow leak, where $Q_{Total\_Leak(n)}=K \times (P_{o(n)})^m$, PF(n) is a value of the peak flow waveform set by an operator, K is the conductance for the equivalent orifice representing the total gas flow leak, Po is the pressure at the pertinent pressure site where the leak is assumed to be located, Ctube is Tubing compliance, and Py is tubing circuit wye pressure.

5. A computer implemented program adapted for performing the steps of the method according to claim 1.

6. A system for calculating, in real-time, an amount of gas during breath delivery, the system comprising:

a Patient-Tubing system coupled with an outlet of a gas delivery system for conveying gas to a patient during gas-supplemented inhalations;

a flow sensor coupled with said outlet for sensing the gas flow;

a Patient-Tubing system pressure sensor coupled with said Patient-Tubing system for sensing gas pressure therein and providing Patient-Tubing system pressure signals representative thereof; and a processor coupled with said sensors and operable for receiving said signals therefrom, wherein said processor is configured to: (if) obtain, in each of a plurality of sample intervals, flow information from said flow sensor, wherein each sample interval is a breath; (ii) obtain, from each of the plurality of sample intervals, pressure information from said Patient-Tubing system pressure sensor; (iii) calculate for the one sample interval, based on a compliance of the tubing and a calculated derivative of the pressure information from the Patient-Tubing system pressure sensor, a Patient-Tubing system flow; and (iv) continuously calculate for each of the plurality of sample intervals, based on the calculated Patient-Tubing system flow and on the flow information from the flow sensor, the amount of gas needed to compensate for gas lost in pressurization of the Patient-Tubing system and gas lost through leakages in the Patient-Tubing system;

wherein the compensation comprises the equation $Q_{tube}=C_{tube} \times dP_y/dt$, where $Q_{tube}$ is Tubing gas flow, $C_{tube}$ is Tubing compliance and $P_y$ is tubing circuit wye pressure; and wherein calculating the amount of gas needed to compensate gas loss comprises determining an estimate for leakages in the patient-tubing system, which comprises the tubing circuit, the patient's airways and the patient's lungs, wherein compensation for flow lost due to leakages in the tubing system and/or the airway and/or the lung utilizes conductance for the equivalent orifice representing the tubing circuit leak and/or the lung leak and/or the total gas flow leak.

7. The system according to claim 6, wherein the processor comprises a signal processor and a general processor, and wherein the signal processor is configured to obtain signals from the flow sensor and the Patient-Tubing system pressure sensor, and further wherein the general processor are configured to perform said calculations.

8. The system according to claim 6, further comprising an input unit configured to receive a target gas flow, and wherein the processor is configured to calculate the amount of gas needed to compensate gas loss including determining compensation to reach said target gas flow.

9. A computer implemented method adapted to calculate an amount of gas during ventilation of a patient using the system of claim 6.

* * * * *